United States Patent [19]

Hostettler et al.

[11] Patent Number: 4,584,191

[45] Date of Patent: Apr. 22, 1986

[54] HAIR CARE AND SKIN CARE COMPOSITIONS CONTAINING BIOTIN ETHYL ESTER

[75] Inventors: Hans U. Hostettler, Arlesheim; Bruno Poncioni, Muttenz, both of Switzerland

[73] Assignee: Hoffmann-La Roche Inc., Nutley, N.J.

[21] Appl. No.: 446,116

[22] Filed: Dec. 2, 1982

[30] Foreign Application Priority Data

Dec. 10, 1981 [CH] Switzerland .......................... 7897/81

[51] Int. Cl.[4] ...................... A61K 7/075; A61K 7/06; A61K 7/48
[52] U.S. Cl. ......................................... 424/70; 424/47; 424/71; 424/72; 424/74; 424/DIG. 4; 548/303
[58] Field of Search ............. 548/303; 424/70, 273 R; 514/387

[56] References Cited

U.S. PATENT DOCUMENTS 3,978,084  8/1976  Confalone et al. .............. 424/273 R
4,054,740  10/1977  Field .................................... 548/303
4,284,788  8/1981  Hohenlohe-Oehringen et al. ......................................... 548/303

OTHER PUBLICATIONS

Settel, Drug and Cosmetic Industry 1977, No. 10, pp. 34–37, 156, 158.
Riechestoffe, Aromen, Körperpflegemittel, 1973, No. 7/8, p. 242.

*Primary Examiner*—Richard A. Schwartz
*Assistant Examiner*—Kurt G. Briscoe
*Attorney, Agent, or Firm*—Jon S. Saxe; George M. Gould; John J. Maitner

[57] ABSTRACT

Biotin esters, namely biotin $C_{2-4}$-alkyl esters, are prepared by esterifying biotin with a $C_{2-4}$-alkanol. These esters have the capability of being absorbed by the human skin better than biotin and are converted into biotin during or after absorption. Since biotin itself promotes the fat and cholesterol synthesis of the skin, the novel biotin esters of this invention are useful as active ingredients for cosmetic hair-care and skin-care compositions.

5 Claims, No Drawings

HAIR CARE AND SKIN CARE COMPOSITIONS CONTAINING BIOTIN ETHYL ESTER

SUMMARY OF THE INVENTION

This invention relates to biotin esters of the formula

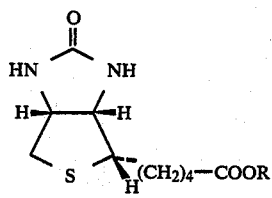

wherein R is $C_{2-4}$-alkyl.

This invention also relates to a process for preparation of such compounds, to cosmetic hair-care and skin-care compositions containing these compounds and to methods for care of the hair or of the skin.

DETAILED DESCRIPTION OF THE INVENTION

The topical use of biotin (D-cis-hexahydro-2-oxo-thieno[3,4-d]imidazole-4-valeric acid) in promotion of the fat and cholesterol synthesis of skin, is well known. These findings have aroused the interest of the cosmetics industry. However, it has been found that the absorption of biotin by the human skin is insufficient in order to achieve satisfactorily the desired effects.

In accordance with the present invention, it has now been found that certain esters of biotin, namely the $C_{2-4}$-alkyl esters of biotin, when used externally are absorbed better by the skin than biotin itself, but are converted into biotin during or after the absorption under the influence of the human organism.

The compounds of the present invention are the $C_{2-4}$-alkyl esters of biotin, i.e. compounds of the general formula

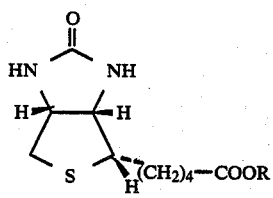

wherein R is $C_{2-4}$-alkyl. These compounds are useful as hair-care and skin-care agents.

The invention also relates to a process for the preparation of the compounds of formula I, cosmetic hair-care and skin-care compositions containing compounds of formula I, the preparation of such compositions as well as a method for the care of the hair or of the skin.

As used herein, the term "alkyl" includes not only straight-chain but also branched-chain alkyl groups. Accordingly, "$C_{2-4}$-alkyl" includes ethyl, n-propyl, isopropyl, n-butyl, isobutyl, sec.butyl and tert.butyl. The preferred alkyl group is ethyl and an especially preferred compound of formula I is biotin ethyl ester.

The compounds of formula I are prepared by esterifying biotin, i.e. the compound of the formula

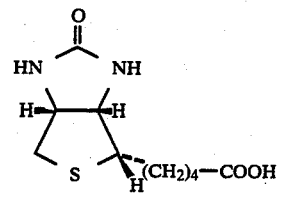

with a $C_{2-4}$-alkanol.

The esterfication can be carried employing conventional procedures well known to one skilled in the art. The esterification is conveniently carried out in suspension in the corresponding $C_{2-4}$-alcohol which is used as the reagent. The esterification is conveniently carried out in the presence of acidic catalysts, especially of acids. Examples of acids which can be utilized in the esterification reaction are sulfuric acid, hydrochloric acid and arylsulfonic acids such as p-toluenesulfonic acid. P-toluenesulfonic acid is an especially preferred acidic catalyst. The esterification is conveniently carried out in a temperature range between room temperature and the reflux temperature of the reaction mixture, preferably the reaction is carried out at the reflux temperature of the reaction mixture.

The compounds of formula I can be isolated and purified according to conventional procedures known in the art.

As noted above, the biotin esters of formula I are better absorbed by the skin than biotin and are then converted into biotin under the influence of the human organism. Moreover, the esters are generally more readily soluble than biotin in aqueous alcohols which are typical solvents or suspension media for cosmetic hair-care and skin-care compositions. This increased solubility is evident from the following Table:

TABLE

| | Solubilities (g/100 g) in aqueous rectified alcohol* | | |
| | Weight ratio rectified alcohol:water | | |
| Compound | 4:6 | 2:8 | 1:9 |
|---|---|---|---|
| Biotin | 0.15 | 0.04 | 0.03 |
| Biotin ethyl ester | >4 | 1.4 | 0.7 |
| Biotin n-propyl ester | 1.9 | 0.5 | 0.4 |
| Biotin n-butyl ester | 1.3 | 0.2 | 0.07 |
| Biotin isobutyl ester | 1.2 | 0.2 | 0.15 |

*95% ethanol

In practice these results indicate that the biotin esters of the present invention can be used in cosmetic compositions in higher application concentrations than biotin itself.

The cosmetic compositions, particularly hair-care and skin-care compositions, of the present invention contain in addition to the active ingredient, i.e., at least one compound of formula I, a cosmetically acceptable carrier suitable for application to the hair or skin. Such carriers include, for example, hair lotions and dressings, e.g. gells, shampoos, hair sprays, hair creams, and skin creams.

The cosmetic compositions of the present invention may contain conventional additives used in hair-care and skin-care formulations. Such additives include, for example, solvents or dispersion media such as water and alcohols (e.g. ethanol); cosmetic bases such as those having greasifying properties; emulsifiers or solubilizers; tensides as wetting agents, dispersants or cleansing substances; thickening agents; biocidal preserving agents; stabilizers such as UV-absorbers and antioxidants; perfumes; colorants; skin-nutrient or hair-nutrient agents; bactericidal agents; deodorants; agents for increasing the skin metabolism or the skin elasticity; and agents for the treatment of dermatoses.

If the cosmetic hair-care or skin-care compositions of this invention are present in the form of sprays, then all carrier gases which are conventional in aerosol mixtures, for example, halogenated hydrocarbons, can be used.

The cosmetic hair-care or skin-care compositions of the present invention contain in general from about 0.01% to about 5.0% by weight, preferably from about 0.1% by weight to about 0.5% by weight of the active ingredient or active ingredients of formula I.

The cosmetic hair-care and skin-care compositions of the present invention are prepared by incorporating at least one of the compounds of formula I into the carrier formulations, optionally containing the above-noted additives, by procedures conventional in the art of cosmetic compounding. Mixing of the ingredients can be carried out in a single step or in several steps.

The cosmetic hair-care of skin-care compositions of the present invention are used by applying an effective amount of the cosmetic hair-care or skin-care composition to the scalp or skin to be treated, for example, by rubbing in or spraying.

The following Examples serve to illustrate the invention in more detail.

EXAMPLE 1

The following procedure is illustrative of the synthesis of compounds represented by formula I.

100 g of biotin were introduced into 2 l of absolute ethanol and treated while stirring with a solution of 12.2 g of p-toluenesulfonic acid in ethanol. Thereafter the mixture was heated at reflux temperature for 4 hours while stirring, the resulting solution is cooled in an ice-bath and the white precipitate filtered off.

An additional amount of precipitate formed upon concentrating the solution and subsequently cooling. The combined white precipitates were then suspended in water, treated with sodium hydroxide up to a pH-value of 7.0 and finally filtered off. The reaction product was dried at 40° C. in vacuo to yield biotin ethyl ester as a white powder, m.p. 124°–125° C.; yield 80 g.

Microanalysis ($C_{12}H_{20}N_2O_3S$):

|  | % C | % H | % N | % S |
|---|---|---|---|---|
| Calculated: | 52.92 | 7.40 | 10.29 | 11.77 |
| Found (anhydrous) | 52.75 | 7.68 | 10.27 | 11.82 |

The following biotin esters were prepared in an analogous manner:
(a) Biotin n-propyl ester, m.p. 124° C.,
(b) Biotin n-butyl ester, m.p. 120°–121° C.,
(c) Biotin isobutyl ester, m.p. 124° C.

EXAMPLE 2

A hair lotion was prepared with the following formulation:

| Active ingredient of formula I (e.g. biotin ethyl ester) | 0.50 g |
|---|---|
| Uvinul ® D 50 (2,2'4,4'-tetrahydroxybenzophenone) (1) | 0.05 g |
| Diisopropyl adipate | 0.20 g |
| Cremophor ® RH 60 (ethoxylated hydrogenated castor oil) (1) | 0.10 g |
| Perfume | 0.10 g |
| Rectified alcohol (95% ethanol) | 45.00 g |
| D-Panthenol ethyl ether | 0.15 g |
| Colorant | (amount as required) |
| Demineralized water ad | 100.00 g |

The rectified alcohol was placed in a stainless steel mixing vessel provided with a propeller stirrer. Thereafter the active ingredient, the Uvinul ® D 50, the diisopropyl adipate, the Cremophor ® RH 60 and the perfume were added and brought into solution with vigorous stirring. Then a solution of the D-panthenol ethyl ether and optionally also the colorant in demineralized water was added and the mixture was stirred until it is homogeneous. In this manner there was obtained a clear or optionally colored solution which is suitable as a hair lotion.

EXAMPLE 3

A clear shampoo was prepared with the following formulation:

| Active Ingredient of formula I (e.g. biotin ethyl ester) | 0.50 g |
|---|---|
| Texapon ® ASV (mixture of fatty alcohol ether sulphates) (2) | 25.00 g |
| Phenonip ® (mixture of p-hydroxybenzoic acid esters dissolved in 2-phenoxyethanol) (3) | 0.50 g |
| D-Panthenol ethyl ether | 0.50 g |
| D-Panthenol | 0.50 g |
| 1,2-Propylene glycol | 1.00 g |
| Cetiol ® HE (polyol polyether-fatty acid ester) (2) | 1.00 g |
| Tego ®—betaine L 7 [N—(3-acylamidopropyl)-N,N—dimethylammonioacetates](4) | 20.00 g |
| Sodium chloride (pure) | 0.50 g |
| Perfume | (amount as required) |
| Colorant | (amount as required) |
| Demineralized water ad | 100.00 g |

The Texapon ® ASV, the Phenonip ®, optionally the perfume, as well as a quarter of the required amount of water were placed in a heatable, stainless steel mixing vessel provided with a stirrer, scrapers, a counter-stirrer and a thermometer. The mixture was warmed to 45° C. while stirring slowly. The active ingredient was subsequently added and brought into solution while stirring at 45° C. and thereafter the heating was terminated.

The D-panthenol ethyl ether, the D-panthenol, the 1,2-propylene glycol, the Cetiol ® HE and optionally the colorant were dissolved together in about 85% of the remaining amount of water while stirring. Thereafter the Tego ® -betaine L 7 was added, and the mixture was stirred homogeneous. The solution obtained was added to the batch in the mixing vessel.

The sodium chloride was dissolved in the remaining amount of water and the resulting, about 10 percent solution was added to the batch in the reaction vessel. The contents of the vessel were then stirred homogeneous and cooled to room temperature. A clear, optionally colored and/or perfumed shampoo was obtained.

EXAMPLE 4

An oil/water cream (skin cream) was prepared with the following formulation:

| | |
|---|---|
| Active ingredient of formula I (e.g. biotin ethyl ester) | 0.50 g |
| Tagat ® S (polyoxyethylene glycerine monostearate) (4) | 3.00 g |
| Glycerine monostearate | 2.00 g |
| Stearyl alcohol | 1.00 g |
| Ethyl adipate | 8.00 g |
| PCL liquid (mixture of alkyl-branched fatty acid esters) (5) | 2.00 g |
| Deltyl-Extra ® (isopropyl myristate) (6) | 3.00 g |
| Cetiol ® HE (polyol polyether-fatty acid ester) (2) | 2.00 g |
| Aquaphil ® K (mixture of lanolin and lanolin derivatives) (7) | 1.00 g |
| Carbopol ® 940 (polyacrylic acid) (8) | 0.40 g |
| Sodium hydroxide (pure) | 0.04 g |
| D-Panthenol ethyl ether | 0.50 g |
| D-Panthenol | 2.00 g |
| Phenonip ® (mixture of p-hydroxybenzoic acid esters dissolved in 2-phenoxyethanol) (3) | 0.80 g |
| 1,2-propylene glycol | 5.00 g |
| Perfume | amount as required |
| Demineralized water ad | 100.00 g |

(a) Preparation of the aqueous phase:

About 90% of the required amount of water, the 1,2-propylene glycol and the Phenonip ® were added at room temperature to a stainless steel vessel provided with an anchor stirrer, scrapers, a second counter-flow stirrer, a thermometer and a built-in homogenizer. The Carbopol ® 940 was sprinkled on and dispersed while stirring. The contents of the vessel were left to steep for 16 hours, thereafter heated to 80° C. and homogenized until all Carbopol ® clumps present had disappeared. A 10 percent aqueous solution of the sodium hydroxide was subsequently added, and the mixture was stirred homogeneous at 80° C. to yield the aqueous phase.

(b) Preparation of the fatty phase:

A mixture of Tagat ® S, glycerine monostearate, stearyl alcohol, ethyl adipate, PCL liquid, Deltyl-Extra ®, Cetiol ® HE, Aquaphil ® K and the active ingredient was heated to 80° C. in a stainless steel melting vessel equipped with an anchor stirrer, scrapers and a thermometer and melted with slight stirring to yield a clear melt (the fatty phase).

(c) Completed Skin Cream:

The fatty phase was added to the aqueous phase, and the mixture was subsequently homogenized for about 10 minutes and further stirred at 80° C. for 30 to 60 minutes. Thereafter, the mixture was cooled to room temperature within about 1 hour, during which the D-panthenol ethyl ether, the D-panthenol and, optionally, the perfume, dissolved in the remaining amount of water, were added at 45° C. to yield a white homogeneous emulsion which is suitable as a skin cream.

Manufacturers of ingredients (1)–(8) used in the Examples are listed below:

(1) BASF, 6700 Ludwigshafen/Rhein, W. Germany
(2) Henkel KGaA, Düsseldorf, W. Germany
(3) Nipa Laboratories Ltd., Industrial Estate, Treforest, South Wales, GB
(4) Th. Goldschmidt AG, D-4300 Essen 1, W. Germany
(5) Dragoco GmbH, D-3450 Holzminden, W. Germany
(6) Givaudan & Cie, CH-1214 Vernier-Geneva, Switzerland
(7) Westbrook Lanolin Company, Argonaut Works, Laisterdyke, Bradford, Yorkshire, GB
(8) B. F. Goodrich Chemical Corporation, 3135 Euclid Avenue, Cleveland, Ohio 44115, U.S.

We claim:

1. A cosmetic composition in the form of a hair lotion comprising from about 0.01% to about 5.0% by weight of biotin ethyl ester in combination with a compatible carrier material.

2. A cosmetic composition in the form of a shampoo comprising from about 0.01% to about 5.0% by weight of biotin ethyl ester in combination with a compatible carrier material.

3. A cosmetic composition in the form of a skin cream comprising from about 0.1% to about 5% by weight of biotin ethyl ester in combination with a compatible carrier material.

4. A method for the care of the hair which method comprises applying an effective amount of the cosmetic composition according to claim 1 to the hair.

5. Method for the care of the skin, which method comprises applying an effective amount of a cosmetic composition according to claim 3 to the skin to be treated.

* * * * *